United States Patent [19]

Kliegman

[11] 4,191,555

[45] Mar. 4, 1980

[54] MONAZA AMIDES AND AMINES AS ETHYLENE INHIBITORS

[75] Inventor: Jonathan M. Kliegman, Wayne, N.J.

[73] Assignee: GAF Corporation, New York, N.Y.

[21] Appl. No.: 924,741

[22] Filed: Jul. 14, 1978

[51] Int. Cl.² .................................................. A01N 5/00
[52] U.S. Cl. ................................................ 71/95; 71/94; 71/127
[58] Field of Search ............................................ 71/95

[56] References Cited

U.S. PATENT DOCUMENTS 3,883,342    5/1975    Abramitio et al. ................... 71/76

OTHER PUBLICATIONS

U.S. Pat. 2,961,798, Chem. Abst., vol. 55 (1971) 4871d.
Kukalenko et al., Chem. Abst., vol. 79 (1973) 39335u.
Takahashi et al., Chem. Abst., vol. 84 (1976) 85633r.

Primary Examiner—Catherine L. Mills
Attorney, Agent, or Firm—Walter C. Kehm; Marilyn J. Maue

[57] ABSTRACT

Monaza amines and/or amides having a 5 membered ring containing 4 carbon atoms or a 6 membered ring containing 5 carbon atoms, in which the nitrogen atom is bonded to hydrogen, alkyl of from 1 to 3 carbon atoms or hydroxyalkyl of from 1 to 3 carbon atoms; which compounds function as agents for inhibiting in vivo formation of ethylene in plant biochemical processes.

9 Claims, No Drawings

MONAZA AMIDES AND AMINES AS ETHYLENE INHIBITORS

BACKGROUND OF THE INVENTION

The role of ethylene in plant biology has been the subject of numerous studies for over 50 years (see Ethylene in Plant Biology by F. B. Abeles, Academic Press, 1973). While in certain cases, the effects of ethylene are highly desirable at certain stages of plant development, it is also beneficial in other stages to inhibit and/or in some way monitor the extent of such effects in plant development.

Since ethylene is a naturally occurring hormone in plants, its hormonal influence is always present. However, ethylene effects are often magnified beyond desirable limits by stress situations such as trauma caused by application of chemicals, insect damage, temperature extremes, drought, γ-irradiation, disease, mechanical wounding, unfavorable biological environment or other phenomena which stimulate the plant's natural metabolism to form an increased supply of this hormone. Generally, older plant tissue has less tolerance for contact with foreign chemicals than young tissue so that a phytotoxic affect, evidenced by increased ethylene production, is more easily induced. Young tissue, which is less specialized exhibits significantly higher dosage tolerances before triggering the plant's defence mechanism to counteract the influence of foreign chemicals.

Some of the deleterious effects on plants caused by ethylene imbalance include premature breaking of seed, bud, tuber, corm or bulb dormancy; the stimulation of fungal spore germination and increased growth rate of molds; leaf abnormalities and hypertrophy of cortex tissue; spoilage of picked fruit; abortion of fruit and flower buds; unseasonal ripening of fruits; leaf senescence; the reduction of protein levels and immature development of fruit; rapid defoliation which results in plant morphology; and many more which are extensively described in numerous publications and texts. The above are only a few of the undesirable effects resulting from an inordinate supply of ethylene in the plant.

Departure from the normal levels of hormones and proteins in plant cells, such as may be experienced due to stress, induced, e.g., by a disease or injury situation, can result in secondary changes which deleteriously affect growth and development of the cell and plant. Many of the abnormal developments widely discussed, particularly epinasty and tissue proliferation, are due to such secondary effects caused by such imbalance of the ethylene hormone in plant tissue.

In addition to avoiding the disadvantages caused by stress ethylene production, it is also desirable in certain situations to depress normal ethylene formation in a plant, e.g. to delay normal senescence, defoliation, sprouting, ripening, spoilage of picked fruit or vegetables and to extend the period for crop development before ripening so as to promote a larger, more fully developed produce. Accordingly, it is the aim of present research to provide a method, a chemical or a composition which is capable of closely controlling, blocking and/or monitoring ethylene production in plants to prevent untimely metabolic effects and to generally provide healthy development in the plant while promoting certain desired effects for improved harvesting and yield of high quality crops.

It is an object of the present invention to provide such a compound, capable of closely regulating and altering the rate of in vivo ethylene production and varying plant response wherever applied to meet specific needs.

Another object of the present invention is to provide a process for applying a compound which is biologically non-phytotoxic to plant life.

Still another object of this invention is to utilize a readily available and economical compound for the control of biological effects caused by a plant hormone.

Still another object is to provide a process for significantly preserving the freshness of cut flowers.

Still another object is to provide a treatment which inhibits in vivo generation of ethylene, causing spoilage of picked fruit.

Another object is to regulate ripening of growing crops to obtain maximum size and development and to coincide with the most advantageous season for harvesting so as to avoid damage due to frost or rain and to avoid second and third seasonal harvesting.

These and other objects of the invention will become apparent from the accompanying description and disclosure.

According to this invention, there is provided an agent for inhibiting in vivo ethylene production in plants, said agent being a monaza amine and/or amide represented by the formula:

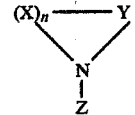

wherein each X is CH or $CH_2$; n is an integer having a value of 3 or 4; Y is CH, $CH_2$ or C=O and Z is hydrogen or alkyl of 1 to 3 carbon atoms which is optionally substituted with a hydroxy group. Of these compounds, those having at least one doubly bonded carbon atom wherein Z is hydrogen or alkyl of 1 to 2 carbon atoms are preferred, and N-methyl-2-pyrrolidone is most preferred.

Representative of the preferred ethylene inhibiting agents of the present invention are N-methyl-2-piperidone, N-(ethyl)-2-pyrrolidone, N-(hydroxyethyl)-2-pyrrolidone, N-ethyl-2-piperidone, 2-pyrrolidone, N-methyl-2-pyrrolidone, N-(hydroxymethyl)-2-pyrrolidone, N-methylpyrrole, N-methylhydroxypiperidone, N-methyl-2-pyridone, N-(ethyl)-2-pyridone, trihydro-N-methyl pyridine, N-methyl-hydropyridine, 2-piperidone, 2-pyridone, N-methylpyrroline, 2-pyrrolone, N-methyl-2-pyrrolone, etc. N-methyl-2-pyrrolidone is the most effective of these chemical agents and is additionally preferred because of its availability, its chemical properties, such as low vapor pressure and freezing point which provide stability over a wide range of climatic conditions, its non-phytotoxic nature and solubility in a wide variety of chemicals which allows for its incorporation in various agricultural formulations, e.g. in combination with a liquid solvent or in more complex compositions additionally including a fungicide, herbicide, nematocide, and/or another active agricultural plant growth regulating chemicals.

Ethylene inhibiting agents such as N-(isopropyl)-2-pyrrolidone, N-methylpiperidine, N-methylpyrrolidine, N-ethylpyrrolidine, e.g. those inhibiting agents which contain no doubly bonded carbon atom or have propyl substituent on the nitrogen, appear to have somewhat limited effect and are recommended only for plants which have not achieved full maturity or young tissue. On mature plants these agents induce a phytotoxic response at acceptable dosage levels so that their use in such cases is not recommended.

Although the heterocyclic compounds of the present invention may be applied directly to the plant, for economic reasons and for better coverage and distribution, the present agents are usually employed in a composition, e.g. mixed with an inert diluent or carrier which is preferably a liquid such as water, xylene, toluene, cyclohexane or other paraffins, a mineral oil fraction, a vegetable oil, or any other conventional and inert organic liquid, or mixtures thereof which are commonly employed as inert extenders in agricultural applications.

For the purposes of the present invention, the concentration of the present inhibiting agent in a composition applied to a plant is within the range of between about 150 ppm and about 5,000 ppm, preferably between about 500 ppm and about 3,500 ppm and most preferably an amount not in excess of about 3,000 ppm. Generally, the inhibiting affect of the present agents is more pronounced in seedlings, usually considered to include plants through the third foliate stage, and least effective in fully developed plants whose vegetative growth increase has substantially ceased. However, since the stress tolerance of older plant tissue varies somewhat with the species of ethylene inhibitor applied, it is recommended that the more active species of the present agents or those which tend to have an irritating influence at certain stages of plant development, be emloyed in a concentration within a lower portion of the above range, so as to avoid a stress situation capable of inducing a phytotoxic influence by temporarily increasing the generation of ethylene. Of the present agents, N-methyl-2-pyrrlidone exerts a consistent inhibitory effect at all concentration levels tested. Those agents which are not preferred perform best at higher dosage levels, e.g., about 2,000 ppm to about 5,000 ppm depending on the age of the plant and the agent selected.

The inhibiting agent is conveniently employed in a composition with an extender. The liquid carrier or extender may optionally contain a convention amount of surface active agent such as a polyoxyalkylene fatty acid ester or alcohol, ether, lignin, methyl cellulose, etc.; although such is not needed to provide the foregoing benefits of this invention. Also, water diluent can be employed with an auxiliary organic solvent which may be selected from those listed above. Thickeners and emulsifiers such as guar gum, locust bean gum, palm oil or latexes and vegetable oils can also be added to prevent removal by rain or other chemical sprays.

It is to be understood, however, that the present N-heterocyclic agent can also be applied to the plant as a powder, e.g. dust or moistened to form a paste, or it can be used as a coarse granulate solid by use of dry extenders such as talc, bentonite, clays, diatomaceous earth, Kaolins and other inert and conventional solid extenders in the same concentration ranges set forth for the liquid carriers.

The present compositions are applied to plants at a rate of between about 0.05 and about 100 Kg/hectare, preferably between about 0.8 and about 15 Kg/hectare of soil area, or in a weight plant dosage between about 0.001 and about 0.2 grams of N-heterocyclic agent per plant to provide the desired inhibition of ethylene generated by the plant.

Plants are treated with the present N-heterocyclic agents at any temperature normally encountered under field conditions and at any time prior to, or after harvesting, depending upon the result to be achieved.

All plants utilize and generate ethylene in the regulation of growth and development; thus, any chemical which inhibits in vivo generation of ethylene will reduce or block the effects resulting from such metabolic generation of ethylene. Specifically, the results of effective treatment with the present inhibitory agents include the following:

1. Delays the spoilage of picked fruit and vegetables and the withering of cut ornamentals.
2. Delays ripening in both growing and harvested crops.
3. Delays loosening and abscission of fruit, nuts and other crops.
4. Promotes resistance to stunting and malformation of foliage in growing crops.
5. Increases the size and weight of fruit and vegetables prior to ripening by extending the growing time.
6. Minimizes sucker formation.
7. Interrupts crop ripening after harvest during transportation to market.
8. Prevents tuber sprouting until planting.
9. Inhibits latex flow in rubber trees during inclement seasons, thereby lengthening the tree life.
10. Retards seed germination and breaking of dormancy.
11. Promotes cell and root elongation and leaf expansion.
12. Prevents underdevelopment of commercial crops and sex reversal in plants.

A substantially complete discussion of effects caused by ethylene is found in many publications, including the text, "ETHYLENE IN PLANT BIOLOGY," by Frederick B. Abeles, Academic Press, Inc., which discusses documented affects of ethylene as early as 1901 and considers particular effects on more than 60 specific varieties of plants.

Having generally described the invention, reference is now had to the accompanying examples which illustrate the specific experimental findings and preferred embodiments. It is to be understood, that these examples are not to be construed as limiting to the scope of the invention which is defined by the accompanying claims.

EXAMPLES 1-20

Determinatin of Ethylene Generation

The ability of the present agents to inhibit ethylene generation was determined by the following procedures.

In a growth chamber maintained at 30° C. and 2,000-3,000 foot candle light, soybean plants from the same seed source were grown to various stages of development. Each of the following experiments were carried out in quadruplicate, and the results (found to be highly reproducible), were averaged and reported in Table I below.

In the following Examples 1-20, a leaf disc sample from, (a) plant seedlings about 2 weeks old (Examples 1-5); (b) underdeveloped plants at the trifoliate stage (Examples 6-9); (c) fully developed plants with no further growth increase (Examples 10-14); (d) a second group of fully developed plants (Examples 15-17); and (e) a third group of fully developed plants (Examples 18-20), were removed by cutting the leaf with a circular cork borer. Each leaf disc sample was immersed for 30 minutes in a 100 milliter aqueous solution containing water as a control or aqueous solutions containing 1,000 ppm and 3,000 ppm of the compound to be tested. At the end of 30 minutes the leaf disc was removed from the solution, patted dry and inserted into a 25 ml glass vial equipped with a septum through which a syringe could be inserted for extracting a sample of the supernatant air above the leaf disc. Examples 1 through 24 were allowed to stand in the light for one hour and Examples 25 through 31 were allowed to stand in the light for 16 hours, after which a gas sample above the leaf in the vial was removed and analyzed for ethylene by gas liquid phase partition chromatography. Comparison with the control, reported in nanoliters of ethylene per liter of air per 10 cm$^2$ of leaf surface, are presented in the following Table (based on an average of 4 replicate samples). For the purpose of comparison, the control was assigned a value of 1.0 and the test compounds were reported as the percent deviation from the control.

Each of the foregoing experiments was repeated, except that the leaf disc samples were similarly treated and held in the dark for the above periods prior to analysis of the gas samples. The results of these experiments are also reported in Table I.

TABLE I

| Ex. No. | TEST COMPOUND | $C_2H_4$ GENERATED, BASED ON CONTROL | | | |
|---|---|---|---|---|---|
| | | 1000 ppm | | 3000 ppm | |
| | | Light | Dark | Light | Dark |
| 1. | Control (water) = 500 nl $C_2H_4$/1/10cm$^2$ | 1.0 | 1.0 | 1.0 | 1.0 |
| 2. | (N-(hydroxyethyl)-2-pyrrolidone | −38% | −25% | −45% | −32% |
| 3. | N-methylpiperidine | −19% | −15% | −84% | −83% |
| 4. | 2-Pyrrolidone | −73% | −69% | −78% | −75% |
| 5. | N-(isopropyl)-2-pyrrolidone | −30% | −15% | −37% | −30% |
| 6. | N-methyl-2-pyrrolidone | −84% | −82% | −91% | −91% |
| 7. | N-methylpyrrolidine | −65% | −53% | −95% | −95% |
| 8. | N-methylpyrrole | −92% | −83% | −97% | −92% |
| 9. | Control (water) = 640 nl $C_2H_4$/1/10cm$^2$/10 cm$^2$ | 1.0 | 1.0 | 1.0 | 1.0 |
| 10. | N-methyl-2-piperidone | −38% | −60% | +150% | +110% |
| 11. | N-methyl-2-pyridone | −50% | −55% | +130% | +115% |
| 12. | N-methyl-2-pyrrolidone | −50% | −65% | −65% | −90% |
| 13. | Control (water) = 640 nl $C_2H_4$/1/10cm$^2$/10 cm$^2$ | 1.0 | 1.0 | 1.0 | 1.0 |
| 14. | N-methyl pyrrolidine | +185% | +250% | +170% | +228% |
| 15. | N-methylpyrrole | −9% | +133% | +185% | +250% |
| 16. | N-(isopropyl)-2-pyrrolidone | +120% | +168% | +128% | +198% |
| 17. | N-(hydroxyethyl)-2-pyrrolidone | −15% | +120% | +185% | +250% |
| 18. | N-methylpiperidine | 0 | +157% | 0 | −25% |
| 19. | 2-pyrrolidone | −40% | −24% | +120% | +166% |
| 20. | N-methyl-2-pyrrolidone | −50% | −50% | −61% | −60% |
| 21. | Control (water) = 640 nl $C_2H_4$/1/10cm$^2$ evolved / 10 cm$^1$ | 1.0 | 1.0 | 1.0 | 1.0 |
| 22. | N-methyl-2-pyrrolidone | −50% | −60% | −20% | −40% |
| 23. | N-(methyl)-2-piperidone | +40% | −50% | +190% | — |
| 24. | N-methyl-2-pyridone | −80% | −50% | −40% | +170% |
| 25. | Control (water) = 500 nl $C_2H_4$/1/10cm$^2$ evolved / 10 cm$^2$ | 1.0 | — | 1.0 | — |
| 26. | N-methylpiperidine | +82% | — | 0 | — |
| 27. | N-methylpyrrolidine | +200% | — | +166% | — |
| 28. | N-(hydroxyethyl)-2-pyrrolidone | 0 | — | +200% | — |
| 29. | 2-pyrrolidone | −40% | — | +104% | — |
| 30. | N-(isopropyl)-2-pyrrolidone | 0 | — | +146% | — |
| 31. | N-methyl-2-pyrrolidone | −50% | — | −46% | — |

It is noted that certain of the heterocyclic agents in the previous table provide an ethylene generating effect at the higher 3,000 ppm concentration and that this effect occurs more often in older plant tissue which has less tolerance for excessive amounts of certain N-heterocyclic agents and therefre an increase marked by the generation of ethylene, is observed as the response to a stress effect induced by the chemical. In these cases, it is also noted that the agent generally reaches an efficacy threshold at a concentration less than 3,000 ppm, e.g. 1,000–2,000 ppm. Specifically, at about 2,000 ppm, a maximum response is obtained and amounts in excess of about 2,000 ppm are unable to provide a further inhibitory improvement; in fact, such additional amounts often induce a stress situation where the opposite result, namely increased ethylene generation, is observed.

The following Table II interprets data from Table I for preferred inhibition agents in terms of % ethylene inhibition per millimole of the N-heterocyclic agent per liter of aqueous treating solution based on the experimental data obtained in light after one hour except where noted.

TABLE II

| Example No. | Derived from Example | $C_2H_4$ Inhibitor | % Inhibition/mmole/1 × 10$^{-1}$ | |
|---|---|---|---|---|
| | | | 1000 ppm | 3000 ppm |
| | | YOUNG TISSUE | | |
| 32 | 2 | N-(Hydroxyethyl)-2-Pyrrolidone | −49.02 | −19.35 |

TABLE II-continued

| Example No. | Derived from Example | C₂H₄ Inhibitor | % Inhibition/mmole/l × 10⁻¹ 1000 ppm | % Inhibition/mmole/l × 10⁻¹ 3000 ppm |
|---|---|---|---|---|
| 33 | 4 | 2-Pyrrolidone | −62.05 | −22.10 |
| 34 | 8 | N-Methylpyrrole | −72.90 | −26.19 |
| 35 | 6 | N-Methyl-2-Pyrrolidone | −83.16 | −30.03 |
| 36 | 10 | N-Methyl-2-piperidone | −42.94 | +56.50 |
| 37 | 12 | N-Methyl-2-pyrrolidone | ″49.50 | −21.45 |
| 38 | 11 | N-Methyl-2-pyridone | −54.50 | +47.23 |
| | | OLDER TISSUE | | |
| 39 | 22 | N-Methyl-2-pyrrolidone | −19.8 | −6.60 |
| 40 | 24 | N-Methyl-2-pyridone | −87.20 | −14.53 |
| 41 | 15 | N-Methylpyrrole | −7.29 | +49.95 |
| 42 | 17 | N-(Hydroxyethyl)-2-Pyrrolidone | −19.35 | +79.55 |
| 43 | 19 | 2-Pyrrolidone | −34.00 | +34.00 |
| 44 | 20 | N-Methyl-2-Pyrrolidone | −49.50 | −20.13 |
| 45 | 29* | 2-Pyrrolidone | −3.40 | +29.47 |
| 46 | 31* | N-Methyl-2-pyrrolidone | −49.50 | −15.18 |

*AFTER 16 HOURS

The following Table III illustrates the effect of time after spraying with the indicated agent on the inhibtion of ethylene. The data for the following experiments were obtained in the light on old tissue, i.e. fully developed plants. The concentration of the agent being tested in all cases was 1,000 ppm in aqueous solution and the results reported in % Inhibition (−) or % Increase (+) ethylene per millimole of N-heterocyclic agent per liter of aqueous solution ×10⁻¹.

TABLE III

| Example No. | C₂H₄ Inhibitor | % Ethylene/mmole/1 × 10⁻¹ 1,000 ppm 1 hour | % Ethylene/mmole/1 × 10⁻¹ 1000 ppm 16 hours |
|---|---|---|---|
| 47 | N-Methylpyrrole | −7.29 | +66.42 |
| 48 | N-(Hydroxyethyl)-2-Pyrrolidone | −19.35 | 0.00 |
| 49 | 2-Pyrrolidone | −34.00 | −3.40 |
| 50 | N-Methyl-2-Pyrrolidone | −49.50 | −49.50 |

On old plant tissue, N-methylpyrrole, ultimately shows a phytotoxic affect. The inhibitory effect of N-(hydroxyethyl)-2-pyrrolidone is dissipated after 16 hours but exhibits no phytotoxic effect thereafter; and 2-pyrrolidone has a lasting inhibitory effect. It is obvious from the foregoing data that N-methyl-2-pyrrlidone exerts a significant ethylene inhibitory effect on plant tissue at both concentration levels tested, in young and in old plant tissue, under conditions of light or dark and that this effect persists at least 16 hours after spraying.

The outstanding performance of N-methyl-2-pyrrolidone is further established by the experimental results of a field study reported in Table IV below. In this study, four groups of three leaves on living soybean plants, which were undergoing senescence, were sprayed to drench with aqueous solutions containing 1,000 ppm, 2,000 1 ppm and 3,000 ppm N-methyl-2-pyrrolidone. A water spray was used as a control. The soybean plants were obtained from the same seed source and were grown under substantially uniform conditions. The sprayed leaves were then sealed in a plastic bag and gas samples were removed from the bag by syringe after one day and after five days. Each of the gas samples was analyzed by gas liquid phase partition chromatography for ethylene content (measured in parts per billion) and the results reported as shown below.

TABLE IV

| Example No. | NMP, ppm | ppb Ethylene 1 day after spray | ppb Ethylene 5 days after spray |
|---|---|---|---|
| 51 | 0 | 39 | 92 |
| 52 | 1,000 | 50 | 2 |
| 53 | 2,000 | 38 | 1 |
| 54 | 3,000 | 36 | 1 |

The results reported in the above table indicate that the inhibitory effect of N-methyl-2-pyrrolidone has even a greater effect on living plants, so that the in vivo generation of ethylene is almost totally arrested.

Following Table V reports data obtained from discs cut from living soybean leaves which were cultured for 30 minutes as set forth in Example 1. After 30 minutes, the air space above the leaf discs were analyzed for ethylene content and the results are reported in following Table V.

TABLE V

| Example No. | NMP ppm | ppb Ethylene Evolved |
|---|---|---|
| 55 | 0 | 51.5 |
| 56 | 1000 | 21.0 |
| 57 | 0 | 30.5 |
| 58 | 1000 | 4.5 |

Inhibition of Typical Effects on Plants Induced by Ethylene

Hastening of boll opening in cotton plants is a typical effect triggered by in vivo generation of ethylene. To test the inhibitory effect of N-methyl-2-pyrrolidone, 4 groups of 12-week old Gossypium hirsuite plants from the same seed source, grown in sterilized soil in 12-inch clay pots under uniformly controlled conditions, were tested in a growth chamber for % of boll opening on treated and untreated plants. The averaged results of 4 plants were reported for each of examples 59 (untreated) and 60 (treated with agent in aqueous solution and sprayed to drench). The weather conditions simulated in the growth chamber were 70° F. day temperature and 55° F. night temperature. The averaged results reported in Table VI are for total boll activity, i.e., boll break from cracked to fully opened and harvestable bolls.

TABLE VI

| Example No. | NMP, ppm | % BOLL ACTIVITY Days After Treatment ||||||| |
|---|---|---|---|---|---|---|---|---|
| | | 1 | 2 | 3 | 4 | 5 | 6 | 7 | 8–14 |
| 59 | 0 | 0 | 0 | 0 | 0 | 0 | 9 | 27 | 45 |
| 60 | 2344 | 0 | 0 | 0 | 0 | 0 | 0 | 0 | 0 |

The above results are to be expected, however, because they indicate the inhibition of a specific ethylene effect. As the above examples establish, in vivo ethylene generation in plants is markedly reduced by treatment with the present compounds.

I claim:

1. The process of inhibiting ethylene generated by a plant, which comprises contacting said plant with an effective amount of the composition of a monaza compound selected from the group of N-methyl-2-pyrrolidone and 2-pyrrolidone and inert carrier therefor.

2. The process of claim 1 wherein the plant is contacted with said composition before reaching full maturity.

3. The process of claim 1 wherein the plant is contacted with between about 0.001 and about 0.2 grams per plant of the monaza compound in the composition.

4. The process of claim 1 wherein the carrier is water.

5. The process of claim 1 wherein the carrier is an organic liquid.

6. The process of claim 1 wherein the carrier is a granulated solid.

7. The process of claim 1 wherein the concentration of said monaza compound in the inert carrier is between about 150 ppm and about 5,000 ppm.

8. The process of claim 1 wherein the concentration of said monaza compound in the inert carrier is between about 500 and about 3,500 ppm.

9. The process of claim 1 wherein the concentration of said monaza compound in the inert carrier is not more than 3,000 ppm.